United States Patent
Blanton et al.

(10) Patent No.: US 10,675,433 B2
(45) Date of Patent: Jun. 9, 2020

(54) SOLENOID CONTROLLED RESPIRATORY GAS DEMAND VALVE

(71) Applicant: MGC DIAGNOSTICS, INC., St. Paul, MN (US)

(72) Inventors: David A. Blanton, Humboldt, TN (US); Charles Peter Howard

(73) Assignee: MGC DIAGNOSTICS CORPORATION, St. Paul, MN (US)

( * ) Notice: Subject to any disclaimer, the term of this patent is extended or adjusted under 35 U.S.C. 154(b) by 622 days.

(21) Appl. No.: 15/605,085

(22) Filed: May 25, 2017

(65) Prior Publication Data
US 2018/0339126 A1   Nov. 29, 2018

(51) Int. Cl.
*A61M 16/20* (2006.01)
*A61M 16/00* (2006.01)
*F16K 31/40* (2006.01)
*A61M 16/10* (2006.01)

(52) U.S. Cl.
CPC ............ *A61M 16/20* (2013.01); *A61M 16/00* (2013.01); *A61M 16/201* (2014.02); *A61M 16/204* (2014.02); *F16K 31/402* (2013.01); *A61M 16/1005* (2014.02); *A61M 16/206* (2014.02)

(58) Field of Classification Search
CPC .... A61M 16/20; A61M 16/20; A61M 16/201; A61M 16/203; A61M 16/204; A61M 16/206; A61M 16/207; A61M 16/1005; F16K 31/40; F16K 31/42; F16K 31/402; F16K 31/404; F16K 31/0641
See application file for complete search history.

(56) References Cited

U.S. PATENT DOCUMENTS

| | | | |
|---|---|---|---|
| 3,423,062 A | 1/1969 | Grayson | |
| 3,921,670 A | 11/1975 | Clippard, Jr. et al. | |
| 4,178,573 A * | 12/1979 | Swanson | H01F 7/1607 251/30.03 |
| 4,336,590 A | 6/1982 | Jacq et al. | |
| 4,686,975 A | 8/1987 | Naimon et al. | |
| 4,706,664 A | 11/1987 | Snook et al. | |
| 5,360,000 A * | 11/1994 | Carter | A61M 16/20 128/204.26 |
| 5,443,062 A | 8/1995 | Hayes | |
| 5,538,026 A * | 7/1996 | Kazi | F16K 31/408 137/1 |
| 5,865,174 A | 2/1999 | Kloeppel | |

(Continued)

FOREIGN PATENT DOCUMENTS

| CN | 103191503 A | 7/2013 |
|---|---|---|
| CN | 203169768 U | 9/2013 |

(Continued)

*Primary Examiner* — Samchuan C Yao
*Assistant Examiner* — Nathan M Le
(74) *Attorney, Agent, or Firm* — Thomas J. Nikolai; DeWitt LLP (57) ABSTRACT

A prior art demand valve has been modified to make it more responsive to persons with impaired oxygen delivery by replacing its sensing diaphragm and associated mechanically actuated valve actuator with a solenoid activated proportional control valve coupled to an analog pressure transducer via a pulse width modulated current driver circuit. The pressure transducer responds to detected pressure changes in a patient's breathing tube.

7 Claims, 5 Drawing Sheets

(56) References Cited

U.S. PATENT DOCUMENTS

| | | | |
|---|---|---|---|
| 6,050,543 A * | 4/2000 | LaGreca | F16K 27/003 251/129.21 |
| 6,076,550 A * | 6/2000 | Hiraishi | F16K 31/0655 137/550 |
| 6,289,890 B1 | 9/2001 | Bliss et al. | |
| 6,457,697 B1 * | 10/2002 | Kolze | F16K 31/404 251/30.02 |
| 6,540,204 B1 | 4/2003 | Carter | |
| 6,631,716 B1 | 10/2003 | Robinson et al. | |
| 6,719,268 B2 * | 4/2004 | Fukano | F16K 7/14 251/129.17 |
| 6,789,539 B2 | 9/2004 | Martinez | |
| 6,910,482 B2 | 6/2005 | Bliss et al. | |
| 7,503,346 B1 | 3/2009 | Clark | |
| 7,509,957 B2 | 3/2009 | Duquette et al. | |
| 8,066,255 B2 * | 11/2011 | Wang | F16K 31/408 251/30.03 |
| 2009/0260631 A1 | 10/2009 | Aubonnet et al. | |
| 2012/0000462 A1 | 1/2012 | Edwards et al. | |
| 2012/0153193 A1 * | 6/2012 | Gu | F16K 1/52 251/28 |
| 2012/0228535 A1 * | 9/2012 | Da Pont | F16K 31/0693 251/129.15 |
| 2013/0206144 A1 | 8/2013 | Ahmad | |
| 2014/0054479 A1 * | 2/2014 | Shen | A61M 16/203 251/129.08 |
| 2015/0007815 A1 * | 1/2015 | Duquette | F04D 25/08 128/202.27 |
| 2015/0328427 A1 | 11/2015 | Cheng | |

FOREIGN PATENT DOCUMENTS

| | | |
|---|---|---|
| CN | 104971451 A | 10/2015 |
| WO | WO2007121773 | 11/2007 |
| WO | WO2008010021 | 1/2008 |

* cited by examiner

SOLENOID CONTROLLED RESPIRATORY GAS DEMAND VALVE

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates generally to respiratory gas demand valves commonly used in administering oxygen to patients having impaired oxygen delivery (HYPOXEMIA) and in administering various test gases during the course of diagnostic tests conducted by pulmonologists and, more particularly, to a respiratory demand valve that is operative to open and deliver the oxygen or a test gas upon detection of a pressure change in an associated patient circuit due to the onset of the inhalation phase of the respiratory cycle and that closes upon detection of the pressure change at the conclusion of the inhalation phase.

II. Discussion of the Prior Art

In the past, demand valves frequently utilized with respiratory test equipment were of a type that are designed for use with scuba diving air supply tanks. While scuba-type demand valves are suitable for use with healthy, robust individuals, they are frequently unsuitable for use with patients that are infirmed or are neonates with limited lung capacity. One object of the present invention is to provide a demand valve that is responsive to modest pressure changes to effect opening and closing to thereby provide a gas flow during inspiration of a person having ventilatory weakness.

Figure 1:
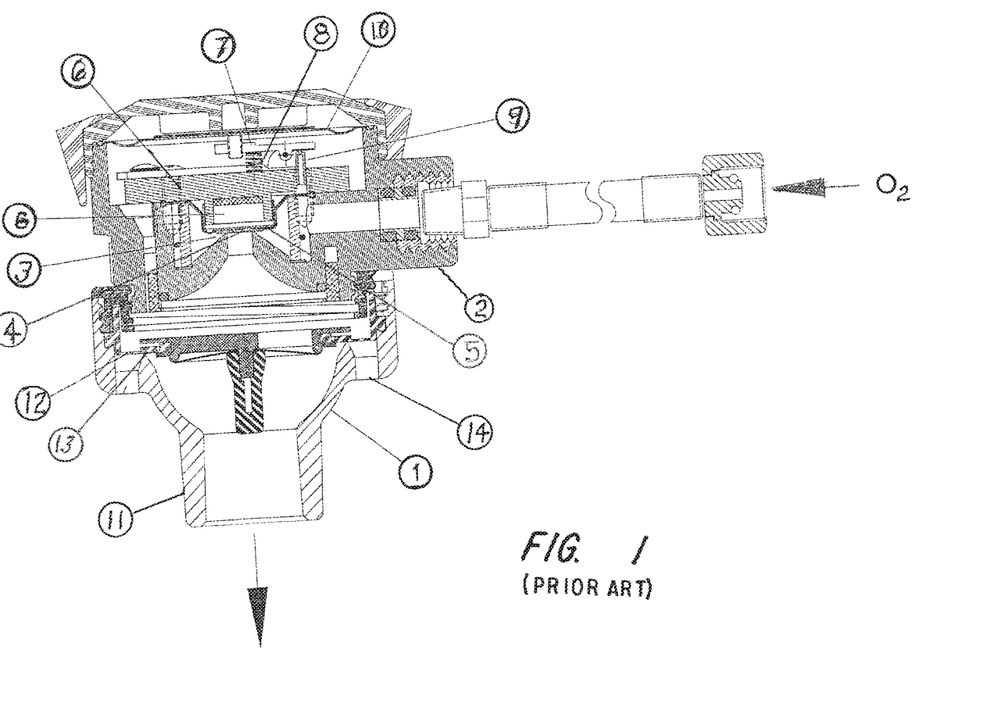
FIG. 1 is a cross-sectional view of a prior art demand valve.

A commercially available demand valve especially designed for administration of oxygen to medical patients is available from Spiracle Technology of Los Alamitos, Calif. A cross-section view of that valve is shown in FIG. 1 hereof. It is seen to comprise a valve body 1 having a supply gas inlet port 2 leading to an interior chamber 3 in which is contained a conical pilot valve seat 4. Diaphragm valve member 5 overlays the conical valve seat 4 and has a small diameter bleed hole formed through it. Also supported within the chamber 3 is a plate 6 on which is pivotally mounted a lever 7 that is urged by a spring 8 to seal a pilot valve 9. A sensing diaphragm 10 cooperates with the lever 4 when a negative pressure is present in an outlet adapter 11 due to a patient's inhaling. Displacement of the sensing diaphragm opens the pilot valve 9. This unbalances the forces acting on the diaphragm 5 so as to lift it off from the conical seat 4, allowing flow of oxygen through the valve's outlet adapter to the patient circuit.

When the patient next begins to exhale, the sensing diaphragm 10 again raises relative to the lever 7 reclosing the pilot valve 9 which pressurizes the diaphragm 5 to again seat it against the conical valve seat 4 and block flow of oxygen through outlet 11.

The Spiracle Technology valve further includes an inhalation/exhalation diaphragm 12 that cooperates with knife edges 13 on the valve's outlet adapter. During exhale, the pressure increase lifts the diaphragm 12 off the knife edges 13 allowing the exhaled gas to flow out a port 14 formed in the outlet adapter.

A chief object of the present invention is to provide a gas demand valve that is practically unnoticeable from a patient standpoint as compared to ambient breathing effort. Mechanically actuated demand valves like the above-described Spiracle valve described above customarily utilize diaphragms to open the valve directly via linkage or indirectly via gas pilot. The deflection and stability of these diaphragms is directly related to the vacuum pressure (less than ambient pressure) being applied to the sensing side of the diaphragm. For the valve to begin opening (crack), the vacuum pressure on the sensing side must overcome the force required to keep the valve closed. The closing force is adjustable by various mechanical means. However, mechanical adjustment for a low cracking pressure results in a greater sensitivity to vacuum pressure variability. An adjustment for a lower sensitivity to vacuum pressure variability results in higher cracking pressure. Efforts to damp the valve operating mechanism to make the valve less sensitive to vacuum variations while maintaining a low cracking pressure results in delayed valve closing (demand gas continues to flow after vacuum has ceased).

SUMMARY OF THE INVENTION

In one embodiment of the present invention, a molded plastic valve body has a supply gas port leading from an exterior surface of the valve body to an interior chamber. A valve seat member is operatively disposed between the interior chamber and a patient circuit outlet port. The valve body also includes a bleed gas exhaust path leading to the patient circuit outlet port.

A valve plate member is sealingly attached to an annular collar on the valve body. The valve plate member includes an upper surface and a lower surface. The lower surface includes an integrally formed nose portion extending outwardly therefrom and centered with respect to the valve seat member. The upper surface of the valve plate includes a cylindrical socket having a first bore that extends from the bottom of the socket and through the nose portion that projects from the lower surface of the valve plate.

A generally circular elastic diaphragm has a peripheral portion captured between the valve body and the valve plate member and overlays the nose portion. This diaphragm includes a bleed port extending through its thickness dimension.

A solenoid-operated proportional valve is mounted on the upper surface of the valve plate member. It includes a cylindrical boss that fits into the cylindrical socket on the upper surface of the valve plate. The solenoid-operated proportional valve also has a displaceable, electrically actuated, poppet for selectively blocking and unblocking a second bore that extends through the boss and leads to the first bore in the valve plate.

In accordance with a further feature of the invention, an electronic pressure transducer is disposed in a patient circuit adapted to be coupled to the patient circuit outlet port of the valve body. The analog output from the pressure transducer is coupled through a pulse width modulated valve driver to the solenoid-operated proportional valve.

The demand valve of the present invention replaces the mechanical sensing diaphragm and the gas port actuation mechanism of a gas pilot style demand valve with an electronic proportional valve. With the proportional valve in place, the operational characteristics of the demand valve are adjusted electronically versus mechanically. The electronic adjustment enables the system to easily adapt to the variability and fluctuation of the sensing vacuum pressure. Common problems associated with mechanical actuation of the demand valve are substantially reduced by actively controlling the opening of the gas pilot port within the proportional valve.

BRIEF DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

Figure 2:
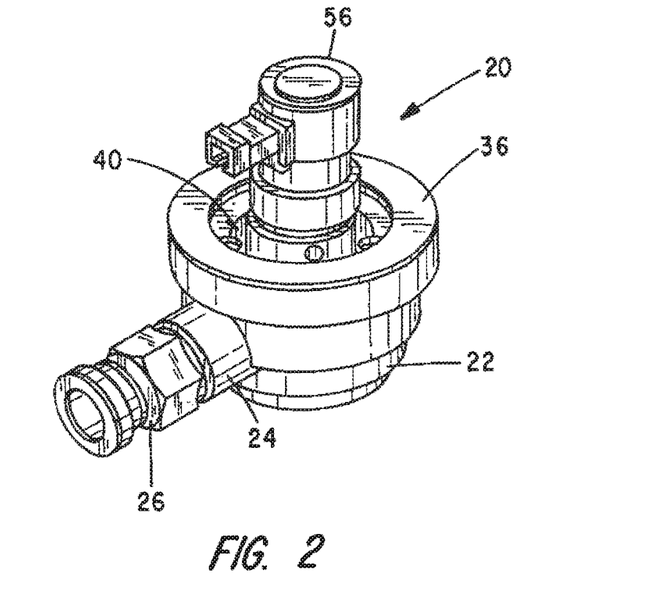
FIG. 2 is a perspective view of a preferred embodiment of the present invention.
Figure 3:
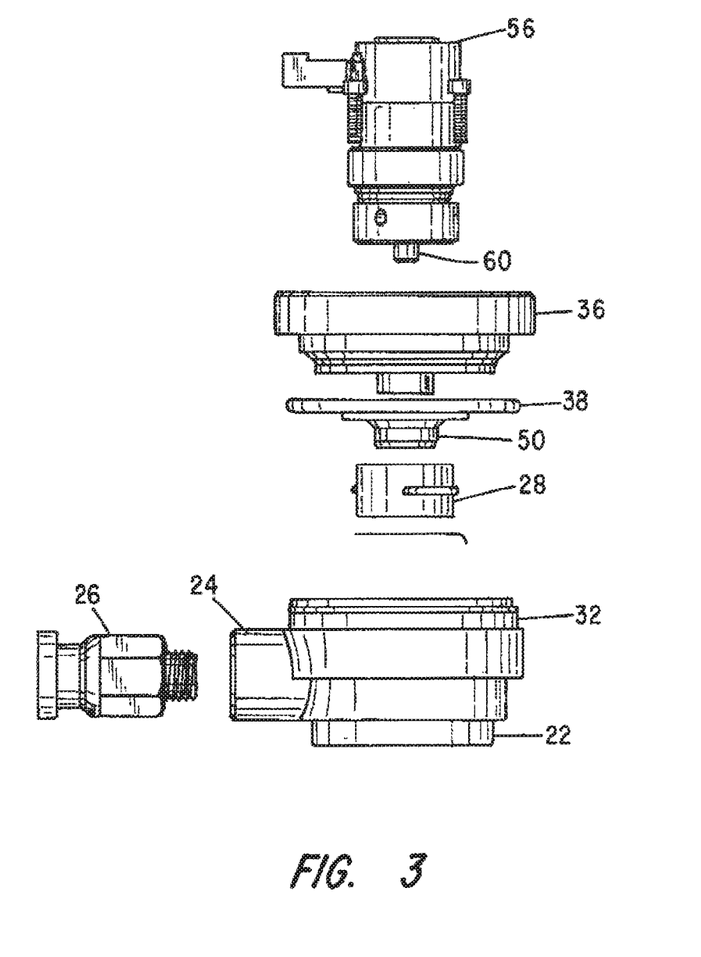
FIG. 3 is an exploded view of the preferred embodiment.

Referring first to FIGS. 1-3, there is depicted the solenoid control respiratory gas demand valve of the present invention. It is indicated generally by numeral 20 and comprises a molded plastic valve body 22 having a supply gas input port 24 with an adapter 26 threaded therein. The adapter 26 permits connection to a respiratory gas supply tank (not shown). The supply port 24 leads to a chamber 27 via a cylindrical filter 28. The valve body 22 includes an integrally molded, generally conical, valve seat member 30, which is centered within the chamber 27 along with an annular collar 32. The valve body further includes a patient circuit outlet port 34 aligned with the valve seat 30.

The solenoid controlled respiratory gas demand valve 20 further comprises a valve plate member 36 that is sealingly attached to the annular collar 32 using an O-ring seal 38. The valve plate member also has a recessed upper surface 40 and a lower surface 42. The lower surface includes an integrally formed, outwardly extending nose portion 44 that is centered with respect to the valve seat member 30. Formed inwardly from the upper surface of the valve plate member 36 is a cylindrical socket 46. A first bore 48 extends from the bottom of the socket 46 through the nose portion 44.

A generally circular, elastic diaphragm 50 has a peripheral portion 52 captured between the valve body 22 and the valve plate member 36 with the elastic diaphragm 50 overlaying the nose portion 44 of the valve plate. Formed through the thickness dimension of the elastic diaphragm is a bleed port 54.

Completing the assembly is a solenoid-operated proportional valve 56 that is suitably mounted on the upper surface 40 of the valve plate member 36. At the lower end of the valve 56 is a cylindrical boss 58 that is designed to fit within the cylindrical socket 46 formed inward from the upper surface 40 of the valve plate member 36. The valve 56 includes an electrically displaceable poppet 60 that cooperates with a second bore 62 that extends through the boss 58 and leads to the first bore 48 formed through the nose 44 of the valve plate member 36. When the solenoid is de-energized, the poppet 60 blocks the bore 62, but when energized, lifts from the position shown in FIG. 4 by an extent that is proportional to the current being delivered to the solenoid valve 56. Without limitation, the solenoid-operated proportional valve 56 may comprise a Clippard EVP series proportional valve available from the Clippard Instrument Laboratory, Inc. of Cincinnati, Ohio. However, limitation to that particular proportional control valve is not intended.

Figure 4:
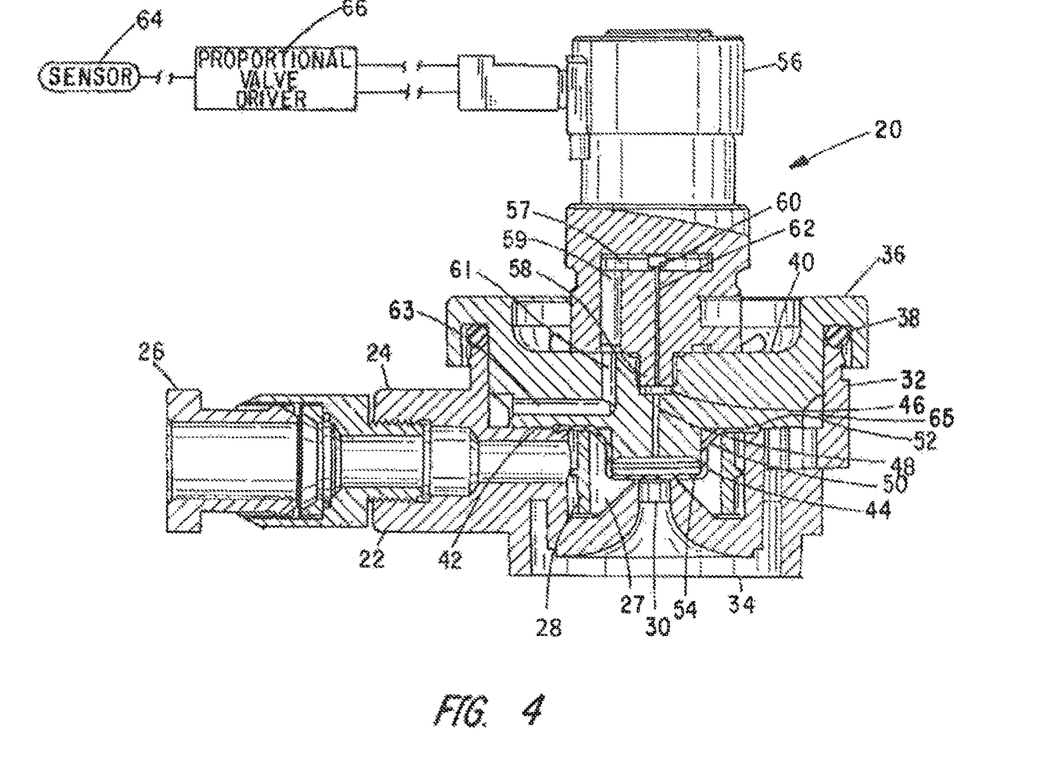
FIG. 4 is a partial cross-sectional view of the preferred embodiment.

The proportional valve 56 has a bleed path including segments 57 and 59 leading to further bleed path segments 61 and 63 formed in the plate 36 that lead to an annular groove 65. The groove 65 is in fluid communication with a port 67 in the valve body 22 leading to the patient circuit outlet port 34.

As earlier mentioned, tubing of a conventional patient circuit joins to the solenoid controlled respiratory gas demand valve at the port 34 and disposed within the patient circuit is a pressure sensor 64 providing an analog output to a proportional valve driver 66. Without limitation, the pressure sensor may comprise an ASDX Series silicon pressure sensor available from the Honeywell Corporation and the proportional valve driver 66 may comprise a EVPD proportional valve driver from Clippard Instrumental Laboratory, Inc. of Cincinnati, Ohio.

Having described the constructional features of the solenoid controlled respiratory gas demand valve 20, consideration will next be given to its mode of operation.

In the absence of an appropriate drive signal from the proportional valve driver 66, the poppet 60 of the solenoid valve 56 is closed against the upper end of the tubular bore 62. Gas under pressure applied through the adapter 26 into the chamber 27 seeps through the small bleed port 54 formed through the diaphragm 50 so that the pressure acting on opposed sides of the diaphragm is equal. With the pressure so equalized, the diaphragm 50 is pressed against the conical seat 30 due to the fact that the effective area of the diaphragm on its upper surface exceeds that on the lower side. Thus, flow of the supply is blocked from flowing out the port 34 and into the patient circuit tubing (not shown). The cylindrical walled filter 28 protects the conical seat 30 and the bleed port 54 from contamination.

As the patient begins to inhale, the pressure sensor 64 detects a drop in pressure from ambient in the patient circuit causing it to issue an analog signal to the proportional valve driver 66 which, in turn, applies a pulse width modulated current proportional to the sensed pressure change to the solenoid valve 56, resulting in a lifting of the poppet 60. As the poppet 60 opens, the gas escapes from the bleed side of the diaphragm 50 through the bores 48 and 62 and the bleed path segments 57, 59, 61, 63 and 65 to the patient circuit outlet port 34. When the flow of the escaping gas is larger than that through the bleed port 54, the pressure on the bleed side of the diaphragm becomes less than that on the inlet gas supply side. This causes the diaphragm to rise off of the conical seat 30, thus allowing the supply gas to flow through the conical seat and into the patient circuit.

Toward the end of the inhalation phase of the patient's respiration, the negative pressure signal is sensed by the sensor 64 in the patient circuit and the opening afforded by the valve 30 decreases as the pressure on the bleed side of the diaphragm 50 begins to increase, thus eventually forcing the diaphragm 50 back onto the conical seat 30 and thereby closing the demand valve.

The distance that the poppet 60 moves relative to the bore 62 is proportional to the negative pressure on the outlet or downstream side of the demand valve. This negative pressure is sensed by means of the electronic pressure sensor 64 which, in turn, is connected to the downstream (patient circuit) side of the demand valve via a length of flexible tubing (not shown) connected to the outlet port 34. The proportional valve driver 66 converts this pressure sensor signal to drive the proportional valve's linear motion. The greater the pressure difference is from the set point, typically ambient, the more the valve seat 30 opens.

Figure 5:
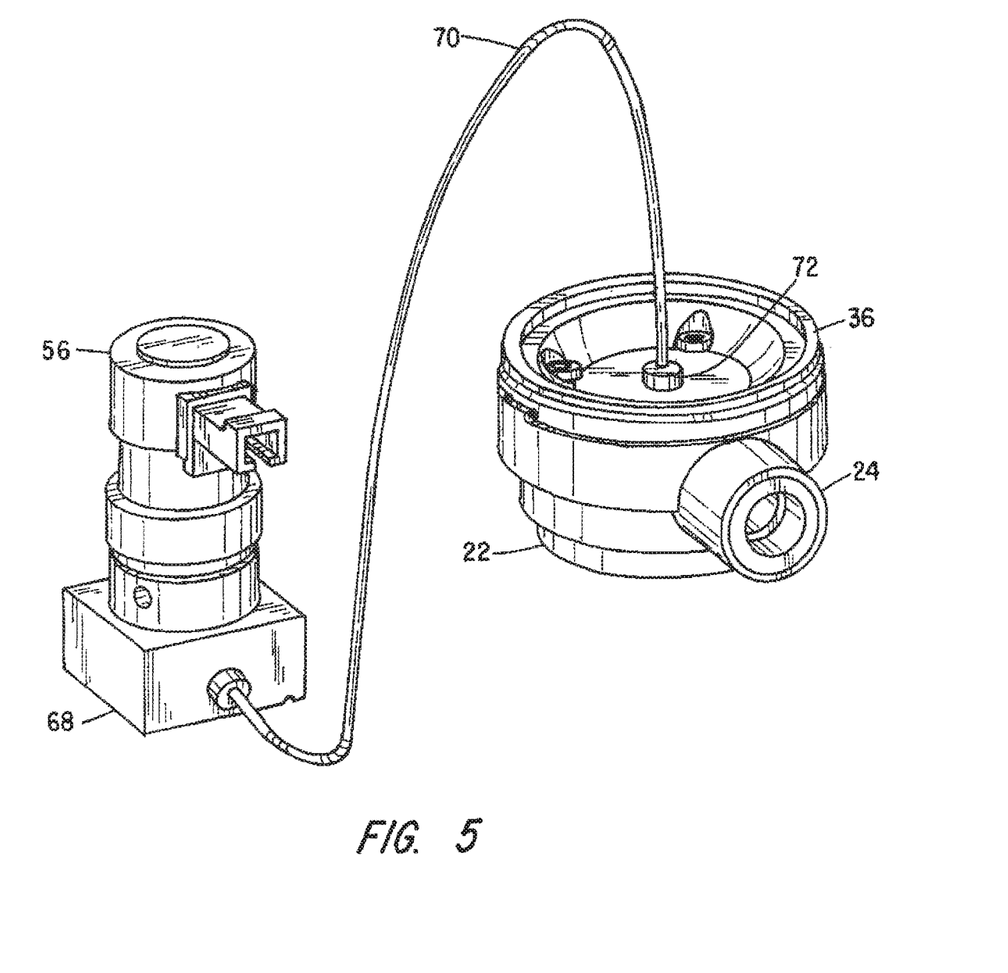
FIG. 5 is a perspective view of an alternative embodiment of the present invention.

In certain applications, it may be desirable to isolate the electronic circuitry from the main gas supply. FIG. 5 illustrates the manner in which the electrically activated solenoid valve 56 can be mounted remotely from the demand valve. In FIG. 5, the solenoid proportional valve 56 is mounted on an adapter block 68 and a length of small diameter tubing 70 extends from the nose 58 and especially the end of the bore 62 in the nose 58 to a fitting 72 which mates the lumen of the tubing 70 to the bore 48 of the plate 36. The tubing 70 preferably has a lumen diameter 0.5-1.0 mm.

The modified prior art Spiracle demand valve described yields a very low cracking pressure with no run on even at maximum flows of about six liters/second when the demand gas pressure is set at 55 psig. Moreover, the solenoid controls of the demand valve is failsafe in that the clippard EVP fails in a closed mode. The operation of the EVP solenoid valve is totally controlled by way of a programmed microprocessor so that various preliminary function tests employing the present invention may be largely software controlled.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A solenoid controlled respiratory gas demand valve comprising:
   a) a valve body having a supply gas port leading from an exterior surface of the valve body to an interior chamber, a valve seat member disposed between the interior chamber and a patient circuit outlet port and a bleed gas exhaust path leading to the patient circuit outlet port, the valve body including an annular collar;
   b) a valve plate member sealingly attached to the annular collar of the valve body, the valve plate member including an upper surface and a lower surface, the lower surface including an integrally formed nose portion extending outwardly therefrom and centered with respect to the valve seat member and the upper surface including a cylindrical socket, there being a first bore extending from a bottom of the socket and through said nose portion;
   c) a generally circular elastic diaphragm having a peripheral portion captured between the valve body and the valve plate member and overlaying said nose portion, the diaphragm including a bleed port extending through a thickness dimension thereof; and
   d) a solenoid-operated proportional valve mounted on the upper surface of the valve plate member, the solenoid-operated proportional valve having a cylindrical boss fitting into said cylindrical socket, the solenoid-operated proportional valve having a displaceable, electrically-actuated poppet for selectively blocking and unblocking a second bore extending through said boss and leading to said first bore in the valve plate.

2. The solenoid controlled respiratory gas demand valve of claim 1 and further including a tubular, gas-permeable, filter member located in the interior chamber of the valve body in surrounding relation to the valve seat member of the valve body and a captured portion of the elastic diaphragm.

3. The solenoid controlled respiratory gas demand valve of claim 1 wherein the solenoid-operated proportional valve and the valve plate member include joined passageways, including the first and second bores, leading from an area surrounding the poppet to the patient circuit outlet port.

4. The solenoid controlled respiratory gas demand valve of claim 1 and further including a supply gas fitting coupled to the supply gas port of the valve body.

5. The solenoid controlled respiratory gas demand valve of claim 3 and further including an electronic pressure transducer disposed in a patient circuit coupled to the patient circuit outlet port of the valve body, the pressure transducer being coupled through a valve driver to the solenoid-operated proportional valve.

6. A solenoid-controlled respiratory gas demand valve comprising:
   a) a valve body having a supply gas port leading from an exterior surface of the valve body to an interior chamber, a valve seat member disposed between the interior chamber and a patient circuit outlet port and a bleed gas exhaust path leading to the patient circuit outlet port, the valve body including an annular collar;
   b) a valve plate member sealingly attached to the annular collar of the valve body, the valve plate member including an upper surface and a lower surface, the lower surface including an integrally formed nose portion extending outwardly therefrom and centered with respect to the valve seat member and the upper surface including a cylindrical socket, there being a first bore extending from a bottom of the cylindrical socket and through said nose portion;
   c) an elastic diaphragm captured between the valve body and the valve plate member and overlaying said nose portion, the diaphragm including a bleed port extending through a thickness dimension thereof; and
   d) a solenoid-operated proportional valve having a displaceable poppet for selectively blocking and unblocking a lumen of an elongated tube joined between the solenoid-operated proportional valve and said first bore.

7. The solenoid-controlled respiratory gas demand valve of claim 1 or claim 6 and further including a pressure sensor mounted to sense pressure within the patient circuit and to produce a DC voltage signal output in response to the sensed pressure, and a pulse width modulated proportional valve driver for connecting the FC voltage signal output of the pressure sensor to the solenoid-operated proportional valve.

* * * * *